United States Patent [19]

Lattrell et al.

[11] Patent Number: 4,746,661
[45] Date of Patent: May 24, 1988

[54] PHENYLPIPERAZINE PROPYLOXYQUINOLINONES AND METHODS FOR SEDATING AND INHIBITING AGGRESSION IN LIVESTOCK THEREWITH

[75] Inventors: Rudolf Lattrell, Königstein; Peter Klatt, Kelkheim; Hermann Gerhards, Hofheim am Taunus; Fritz Bauer, Bad Soden am Taunus, all of Fed. Rep. of Germany

[73] Assignee: Hoechst Aktiengesellschaft, Frankfurt am Main, Fed. Rep. of Germany

[21] Appl. No.: 21,523

[22] Filed: Feb. 26, 1987

Related U.S. Application Data

[63] Continuation of Ser. No. 799,820, Nov. 20, 1985, abandoned.

[30] Foreign Application Priority Data

Nov. 22, 1984 [DE] Fed. Rep. of Germany ....... 3442570

[51] Int. Cl.$^4$ .................. A61K 31/495; C07D 401/12
[52] U.S. Cl. ................................ 514/253; 544/363; 544/373
[58] Field of Search ................ 544/363, 373; 514/253

[56] References Cited

U.S. PATENT DOCUMENTS 4,234,584 11/1980 Lattrell et al. .................. 514/253
4,234,585 11/1980 Winter et al. .................. 514/253

FOREIGN PATENT DOCUMENTS 5089221 7/1980 Japan ........................ 514/253
6122351 9/1981 Japan ........................ 514/253
6164186 12/1981 Japan ........................ 514/253
8083677 5/1983 Japan ........................ 514/253
2017701 10/1979 United Kingdom .

OTHER PUBLICATIONS

Lattrell et al., Chem. Abst. 92-181230t.
Lattrell et al., Chem. Abst. 93-239462j.

Primary Examiner—Donald G. Daus
Assistant Examiner—Cecilia Shen
Attorney, Agent, or Firm—Curtis, Morris & Safford

[57] ABSTRACT

New substituted phenylpiperazine derivatives of the formula I

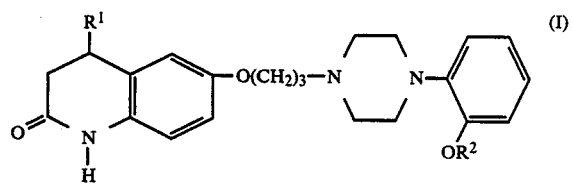

in which $R^1$ and $R^2$ have the indicated meaning, and their physiologically tolerated salts and a process for their preparation are described. The compounds exhibit sedative and aggression-inhibiting effects on livestock. Furthermore, compounds of the formula I'

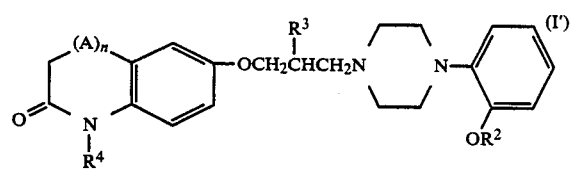

in which n, A, $R^2$, $R^3$ and $R^4$ have the indicated meanings, and their physiologically tolerated salts are claimed for the sedation and inhibition of aggression of livestock.

5 Claims, No Drawings

PHENYLPIPERAZINE PROPYLOXYQUINOLINONES AND METHODS FOR SEDATING AND INHIBITING AGGRESSION IN LIVESTOCK THEREWITH

This application is a continuation of application Ser. No. 799,820, filed Nov. 20, 1985, and now abandoned.

The invention relates to new substituted phenylpiperazine derivatives of the formula I

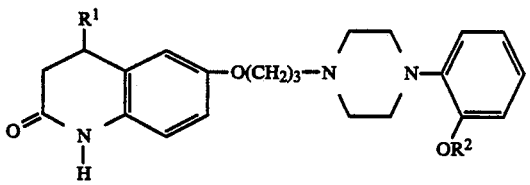

and to their physiologically tolerated salts. The comounds bring about inhibition of aggression of livestock and thus can be used as aggression inhibitors for livestock.

In the formula,
$R^1$ denotes hydrogen or phenyl, and
$R^2$ denotes $C_1$–$C_6$-alkyl, the exception being the simultaneous meaning $R^1$=hydrogen and $R^2$=methyl.

$R^2$ preferably denotes methyl, ethyl, propyl, isopropyl or n-butyl. The compound in which $R^1$ denotes hydrogen and $R^2$ denotes ethyl is particularly preferred.

The invention also relates to a process for the preparation of compounds of the formula I, which comprises
(a) reaction of a compound of the formula II

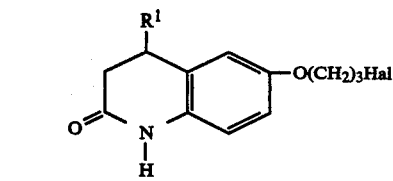

in which
$R^1$ has the abovementioned meaning, and
Hal denotes a halogen atom,
with a phenylpiperazine of the formula III

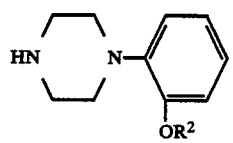

in which $R^1$ has the abovementioned meaning, or
(b) reaction of a compound of the formula IV

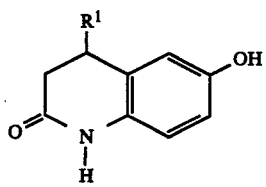

in which $R^1$ has the abovementioned meaning, with a compound of the formula V

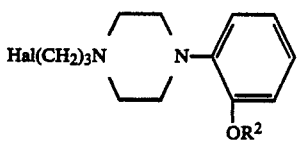

in which Hal and $R^2$ have the abovementioned meaning, or
(c) reaction of a compound of the formula VI

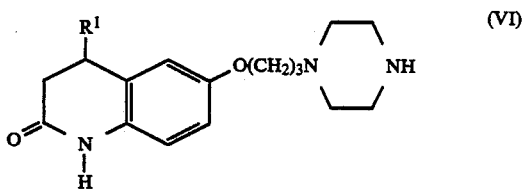

in which $R^1$ has the abovementioned meaning, with a compound of the formula VII

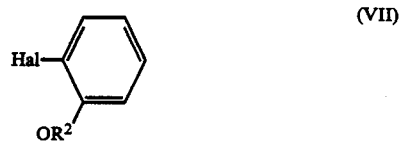

in which Hal and $R^2$ have the abovementioned meaning, or
(d) reaction of a compound of the formula VIII

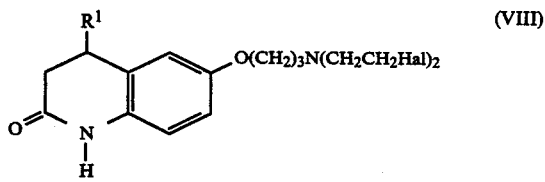

in which Hal and $R^1$ have the abovementioned meaning, with a compound of the formula IX

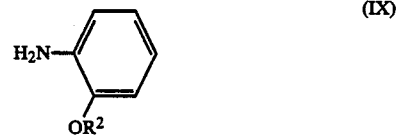

in which $R^2$ has the abovementioned meaning, or
(e) reaction of a compound of the formula X

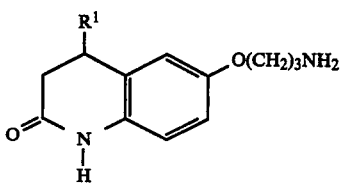

in which $R^1$ has the abovementioned meaning, with a compound of the formula XI

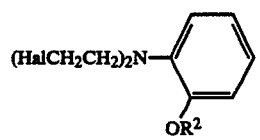

in which Hal and R² have the abovementioned meaning, and, where appropriate, conversion of the reaction products into the physiologically tolerated salts.

According to Process a, the reaction of the 3-halopropoxy compound of the formula II, which is obtained in a manner known per se from the compound of the formula IV and 1,3-dihalopropanes, with a phenylpiperazine of the formula III is preferably carried out in the presence of a base such as sodium hydroxide or potassium hydroxide, sodium carbonate or potassium carbonate, sodium hydride, tertiary amines such as triethylamine, or pyridine, but it is also possible to operate in the absence of a base. The reaction is generally carried out at temperatures between 50° and 200° C., preferably between 60° and 160° C., using from equimolar amounts up to a 5-fold molar excess, preferably equimolar amounts, of the phenylpiperazine of the formula III. If solvents are used, then suitable examples are ethers, such as tetrahydrofuran or dioxane, glycol ethers, such as diglyme, ketones, such as acetone or methyl ethyl ketone, aromatic hydrocarbons, such as toluene, chlorobenzene, alcohols, such as ethanol or isoamyl alcohol, aprotic solvents, such as dimethylformamide or dimethylacetamide, or the like.

According to Process b, the reaction of the phenolic compound of the formula IV with phenylpiperazine derivatives of the formula V is carried out in a manner known per se, the reaction conditions described above preferably being used. One preferred process variant comprises initially converting the phenolic compound of the formula IV into the corresponding alkali metal salt using an alkali metal alcoholate or an alkali metal hydride.

According to Process c, the monosubstituted piperazine derivatives of the formula VI, which in turn are obtained by process variant (a) from compounds of the general formula II and piperazine, are condensed with compounds of the formula VII. The reaction is preferably carried out in a polar solvent, for example alcohols, such as isoamyl alcohol, ethers, such as diglyme, or aprotic solvents, such as dimethylformamide, at temperatures between 60° and 200° C., in the presence of an acceptor for the hydrohalic acid which is formed during the course of the reaction, for example potassium carbonate.

According to Process d, the condensation of the compounds VIII with aniline derivatives of the formula IX is carried out in a solvent, as specified above, at a temperature between 60° and 160° C., preferably in the presence of a hydrogen halide acceptor such as, for example, potassium carbonate or pyridine.

According to Process e, aminopropyl compounds of the formula X, which in turn are obtained in a manner known per se from compounds of the formula II using alcoholic ammonia solution, are condensed with N-(bishalogenoethyl)anilines of the formula XI, the reaction conditions which are used advantageously being those described for Processes c and d.

The compounds according to the invention, of the formula I, are isolated in the free form or as salts, depending on the reaction conditions used. The free base can be converted into its pharmacologically tolerated salts after reaction with inorganic or organic acids. Examples of such acids are hydrochloric acid, sulfuric acid, phosphoric acid, aliphatic, alicyclic, araliphatic, aromatic or heterocyclic carboxylic acids or sulfonic acids, such as acetic acid, tartaric acid, lactic acid, maleic acid, fumaric acid, citric acid, oxalic acid, methanesulfonic acid or hydroxyethanesulfonic acid, or synthetic resins which contain acid groups.

Phenylpiperazine derivatives substituted in the ortho-position of the phenyl radical have already been described (compare European Pat. No. 0,005,828 or U.S. Pat. No. 4,234,584 respectively). The compounds described in these publications exhibit neuroleptic activity.

It has now been found, surprisingly, that the phenylpiperazinopropyloxyquinolinones of the formula I have a sedative and, in particular, aggression-inhibiting effect on livestock. Furthermore, it has been found that the phenylpiperazine derivatives described in U.S. Pat. No. 4,234,584 also exhibit an effect of this type.

Thus, the invention also relates to compounds of the formula I'

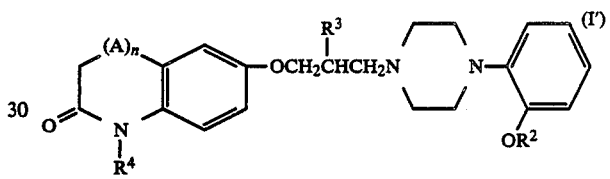

in which
n denotes 0 or 1,
A denotes CH—R¹, R¹ denoting hydrogen or phenyl,
R² denotes $C_1$-$C_6$-alkyl,
R³ denotes hydrogen or, if n is 0, also hydroxyl, and
R⁴ denotes hydrogen or methyl,
and to their physiologically tolerated salts for sedation and inhibition of aggression of livestock.

Furthermore, the invention relates to pharmaceutical products containing a compound of the formula I and its salts, in particular for the sedation and inhibition of aggression of livestock, preferably of hogs.

In particular, the invention relates to products which contain as active compound a compound of the formula I in which R¹ denotes hydrogen and R² denotes ethyl.

The effect of the compounds listed in Table 1 on domestic animals is described below:

TABLE 1

Ortho-substituted phenylpiperazine derivatives

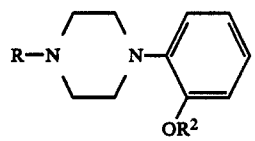

| Compound | R | R² |
|---|---|---|
| 1 | 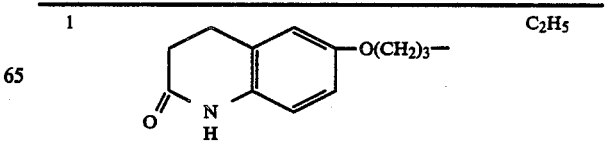 | $C_2H_5$ |

TABLE 1-continued
Ortho-substituted phenylpiperazine derivatives

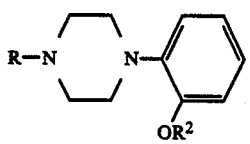

| Compound | R | R² |
|---|---|---|
| 2 | 3,4-dihydro-2(1H)-quinolinone-6-yl-O(CH₂)₃— | CH(CH₃)₂ |
| 3 | 3,4-dihydro-2(1H)-quinolinone-6-yl-O(CH₂)₃— | C₄H₉ |
| 4 | 4-C₆H₅-3,4-dihydro-2(1H)-quinolinone-6-yl-O(CH₂)₃— | CH₃ |
| 5 | 3,4-dihydro-2(1H)-quinolinone-6-yl-O(CH₂)₃— | CH₃ |
| 6 | 1-methyl-2-oxo-indolin-5-yl-OCH₂CH(OH)—CH₂— | CH₃ |
| 7 | 1-methyl-2-oxo-indolin-5-yl-OCH₂CH(OH)—CH₂— | CH₃ |
| 8 | 1-methyl-2-oxo-indolin-5-yl-O(CH₂)₃— | CH₃ |

It emerged from investigations of various species that the abovementioned compounds restrain the affectivity and dynamics of mental processes without at the same time displaying hypnotic or narcotic effects. After administration of the active compounds of the formula I', there is restraint of aggressive behavior of livestock towards members of the same species or towards humans, with general sedation. At the same time the locomotor activity and responsiveness of the livestock are substantially retained.

TESTS ON HOGS

Hogs which are housed in new groups or transferred to new housing are, after having been put together, involved in precedence struggles with one another. These entail injury, loss of weight and a considerable amount of stress, and it is not uncommon for these to result in deaths. If, before they are put together, such hogs are treated, orally or intramuscularly, with one of the compounds described, then the precedence struggles which have been described do not occur or occur only in isolated cases in a mild form. Table 2 below presents the results of the tests, the observation period lasting until 5-7 hours after the treatment.

TABLE 2

| Compound No. in Table 1 | Dose mg/kg | Mode of admin. | Number of hogs treated | Fights per animal | Number of untreated hogs | Fights per animal |
|---|---|---|---|---|---|---|
| 1 | 2.5 | oral | 12 | 0.5 | 12 | 1.3 |
|   | 5.0 | oral | 28 | 0.5 | 28 | 4.2 |
|   | 0.25 | i.m. | 14 | 0.6 | 12 | 2.7 |
|   | 0.5 | i.m. | 9 | 1.8 | 8 | 5.6 |
|   | 1.0 | i.m. | 18 | 0.8 | 18 | 2.5 |
|   | 1.0 | i.m. | 3 | 0 | 3 | 2.3 |
| 2 | 1.0 | i.m. | 3 | 1.7 | 3 | 3.4 |
| 3 | 1.0 | i.m. | 3 | 0 | 3 | 2.8 |
| 4 | 1.0 | i.m. | 8 | 0.6 | 9 | 2.8 |
| 5 | 1.0 | i.m. | 8 | 0.6 | 9 | 2.8 |
| 6 | 1.0 | i.m. | 5 | 0 | 5 | 2.4 |
| 7 | 1.0 | i.m. | 3 | 0.7 | 3 | 2.8 |
| 8 | 1.0 | i.m. | 7 | 0 | 3 | 2.4 |

TESTS ON CATTLE

Two refractory three-year old bulls which could be led only with difficulty were successively led by three experienced attendants from the tying stand with screens to a cattle weighbridge about 50 m away. Here the animals received an i.m. administration of 0.5 mg/kg body weight, in one instance, and 1.0 mg/kg body weight, in the other case, of the compound of Example 1. After 15 minutes, it was possible for both bulls to be led back to the tying stand without difficulty, with no screen, by one attendant in each case. The sedative and antiaggressive effect had disappeared after about 5 hours.

TESTS ON DOGS

The compound of Example 1 was administered i.m. in doses of 0.25, 0.5 and 1.0 mg/kg body weight to groups of three 3 beagle dogs (1 year old). Then the animals were placed in a room with which they were unfamiliar and their behavior was observed continuously up to 5 hours after administration.

0.25 mg/kg dose:

The behavior was normal for up to 10 minutes after the treatment (inspection of the new surroundings). Subsequently the animals showed slight uncertainty of movement, appeared sedated and laid themselves down together for about 30 minutes. They retained reactions to outside noises. After 1 hour there were alternate periods of resting and activity, and the sedative effect had disappeared by 3 hours after administration.

0.5 mg/kg dose:

5 minutes after the treatment there was onset of marked uncertainty of movement, and the animals appeared heavily sedated land they laid themselves down. Their responsiveness was retained. After 45 minutes coordination of movement returned, there were alternate periods of resting and activity. The sedative effect persisted for 3 hours.

1.0 mg/kg dose:

There was onset of extremely pronounced sedation within 3–5 minutes after the treatment. The animals were able to stay on their feet only with difficulty. Some of them stood with their heads lowered and incipient stereotypical movements were detected. Dogs which had lain down (dogs which had laid themselves down with-out outside assistance) which were placed in a dorsal position remained in this position for a prolonged period. Responsiveness had returned after 30 minutes. This was followed by long periods of resting which, after 3 hours, alternated with periods of activity, the movements being normal. The sedative effect began to disappear after 4 hours and was almost completely abolished after 5 hours.

With all three doses no aggression towards members of the same species was seen during the observation period.

TESTS ON CATS

Three castrated ♂ cats (6 years old) which were housed together were treated i.m. with the compound of Example 1 in a dose of 1.0 mg/kg body weight and were left in their cubicle. The observation period lasted 5 hours. There was onset of marked sedation 10 minutes after administration. The animals showed uncertainty of movement and laid themselves down. Their responsiveness was reduced for 1 hour. The cats, which were not tame enough to handle before the treatment, could be placed on a table without difficulty and allowed various examinations to be carried out without making defensive movements. There was a detectable slight tendency to avoidance behavior. The sedative effect flattened off after 4 hours, and had been almost completely abolished after 5 hours.

It is evident from the results of the tests that the compounds display satisfactory dose-dependent sedative and, additionally, antiaggressive effects after oral and parenteral administration to livestock.

The following exemplary embodiments of compounds of the formula I which can be prepared according to the invention serve to illustrate the invention further, but they do not restrict it to them.

EXAMPLE 1

6-[3-(4-Ethoxyphenyl)-1-piperazinyl)propyloxy]-1,2,3,4-tetrahydro-2-quinolinone

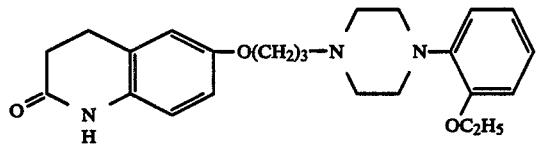

Process a:

Step 1: Preparation of 6-(3-bromopropyloxy)-1,2,3,4-tetrahydro-2-quinolinone:

A mixture of 12.6 g (0.076 mol) of 6-hydroxy-1,2,3,4-tetrahydro-2-quinolinone, 15.8 g (0.115 mol) of potassium carbonate (anhydrous and powdered), 46.5 g (0.23 mol) of 1,3-dibromopropane and 40 ml of N,N-dimethylformamide is stirred at room temperature for 20 hours. 200 ml of water and 100 ml of petroleum ether are added and, after stirring for 1 hour, the precipitate which has formed is filtered off with suction, washed with petroleum ether and dried.

Yield 18.5 g, melting point 100°–106° C. After recrystallization from ethanol, 12.6 g of melting point 116°–117° C. are obtained.

Step 2:

A mixture of 21.2 g (0.074 mol) of 6-(3-bromopropyloxy)-1,2,3,4-tetrahydro-2-quinolinone, 15.3 g (0.074 mol) of 1-(2-ethoxyphenyl)piperazine, 31.2 g (0.223 mol) of anhydrous, powdered potassium carbonate, 1.9 g (0.011 mol) of potassium iodide and 180 ml of toluene is heated under reflux for 23 hours. After allowing to cool, 200 ml of water are added, the phases are separated, and the organic phase is washed twice with water. The solvent is removed in vacuo, and the residue is triturated with ether. The crystalline free base melts at 153°–154° C. It is dissolved in acetone and an excess of ethanolic hydrochloric acid is added. The precipitate which has formed is filtered off with suction, washed with acetone and dried.

Yield: 25.1 g (83% of theory), dihydrochloride of melting point 216° C.

Process b:

0.01 mol of sodium hydride and, after the evolution of gas is complete, 2.8 g (0.01 mol) of 1-chloro-3-[4-(2-ethoxyphenyl)-1-piperazinyl]propane are added to 1.63 g (0.01 mol) of 6-hydroxy-1,2,3,4-tetrahydro-2-quinolinone in 20 ml of dioxane. The mixture is heated under reflux for 10 hours, allowed to cool, diluted with water and extracted with methylene dichloride. After evaporation, ether is added, and the precipitate is filtered off with suction, washed with ether and dried. Melting point 153°–154° C., identical to the compound obtained by process (a).

Process c:

A mixture of 2.9 g (0.01 mol) of 6-[3-(1-piperazinyl)-propyloxy]-1,2,3,4-tetrahydro-2-quinolinone, 1.4 g (0.01 mol) of 2-ethoxyfluorobenzene, 4 g of potassium carbonate and 50 ml of N,N-dimethylformamide is refluxed for 24 hours. After allowing to cool, the mixture is filtered, the solvent is removed in vacuo, and the residue is chromatographed on 200 g of silica gel using methylene chloride/methanol (4:1). The residue from the product fractions is triturated with ether. The compound, of melting point 152°–154° C., is identical to the compound obtained by Process (a).

Process d:

3.5 g (0.01 mol) of 6-[3-(bis(2-chloroethyl)amino)-propyloxy]-1,2,3,4-tetrahydro-2-quinolinone and 4.1 g (0.03 mol) of o-ethoxyaniline in 30 ml of diglyme are heated at 150° C. for 10 hours. The mixture is diluted with water, extracted with methylene chloride, and the solvent is removed in vacuo. A crystalline compound is isolated from the residue by chromatography as described above, and all its properties are identical to that obtained by Processes (a), (b) and (c).

Process e:

A mixture of 2.3 g (0.01 mol) of 6-(3-aminopropyloxy)-1,2,3,4-tetrahydro-2-quinolinone, 2.6 g (0.01 mol) of bis-N,N-(2-chloroethyl)-2-ethoxyaniline, 5 g of anhydrous potassium carbonate and 30 ml of N,N-dimethylformamide is heated at 130° for 10 hours. After allowing to cool, the mixture is diluted with water and worked up as described above. The compound is identical to that obtained by Process a.

The compounds in Table 3 are obtained in analogy to Example 1, Process a, from 6-(3-bromopropyloxy)-

1,2,3,4-tetrahydro-2-quinolinone or 6-(3-bromopropyloxy)-4-phenyltetrahydro-2-quinolinone (Example 4) and the appropriate phenylpiperazine derivatives.

TABLE 3

![Structure]

| Example No. | R¹ | R² | Base (melting point °C.) | Dihydrochloride (melting point °C.) | Yield, % of theory |
|---|---|---|---|---|---|
| 2 | H | CH(CH₃)₂ | 136–138 | 187–189 | 89 |
| 3 | H | C₄H₉—n | 126–127 | 216–217 | 90 |
| 4 | C₆H₅ | CH₃ | 160–161 | 220–222 | 81 |

The compounds in Table 4 are described in U.S. Pat. No. 4,234,584 and they were obtained in accordance with the statements in Examples 35, 1, 12 and 25.

TABLE 4

Example

5.

6.

7.

8.

We claim:
1. A method for the sedation of and inhibition of aggression in livestock, which comprises administering to said livestock an effective amount of a compound of the formula

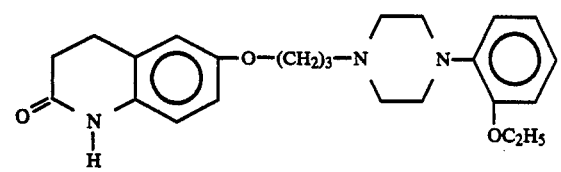

or of a physiologically acceptable salt thereof.
2. A method as in claim 1 wherein said livestock is a pig.
3. A compound of the formula

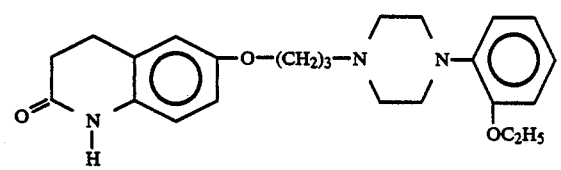

or a physiologically acceptable salt thereof.
4. A pharmaceutical product for the sedation of and inhibition of aggression in livestock containing an effective amount of a compound as in claim 3.
5. A pharmaceutical product in claim 4 wherein said livestock is a pig.

* * * * *